(12) United States Patent
Kakhovsky

(10) Patent No.: US 11,670,406 B2
(45) Date of Patent: Jun. 6, 2023

(54) SYSTEMS AND METHODS FOR REMOVING PERSONAL DATA FROM DIGITAL RECORDS

(71) Applicant: FUJIFILM MEDICAL SYSTEMS U.S.A., INC., Morrisville, NC (US)

(72) Inventor: Dmitry Kakhovsky, Morrisville, NC (US)

(73) Assignee: FUJIFILM MEDICAL SYSTEMS U.S.A., INC., Morrisville, NC (US)

( * ) Notice: Subject to any disclaimer, the term of this patent is extended or adjusted under 35 U.S.C. 154(b) by 219 days.

(21) Appl. No.: 16/862,246

(22) Filed: Apr. 29, 2020

(65) Prior Publication Data

US 2021/0343379 A1 Nov. 4, 2021

(51) Int. Cl.
*G16H 10/60* (2018.01)
*G16H 30/20* (2018.01)
*G06F 21/62* (2013.01)
*G16H 30/40* (2018.01)

(52) U.S. Cl.
CPC ......... *G16H 10/60* (2018.01); *G06F 21/6254* (2013.01); *G16H 30/20* (2018.01); *G16H 30/40* (2018.01)

(58) Field of Classification Search
CPC ... G06F 16/137; G06F 21/6254; G16H 10/60; G16H 30/20; G16H 30/40
USPC .......................................................... 705/2, 3
See application file for complete search history.

(56) References Cited

U.S. PATENT DOCUMENTS

| | | |
|---|---|---|
| 7,047,235 B2 | 5/2006 | Yang et al. |
| 10,037,406 B2 | 7/2018 | Westin et al. |
| 10,037,410 B2 | 7/2018 | Ohad et al. |
| 10,182,073 B2 | 1/2019 | Redlich et al. |
| 10,255,458 B2 | 4/2019 | Aunger et al. |

(Continued)

FOREIGN PATENT DOCUMENTS

| | | |
|---|---|---|
| EP | 3 376 361 A2 | 9/2018 |
| EP | 3 535 927 A1 | 9/2019 |
| WO | WO 2018/085771 A1 | 5/2018 |

OTHER PUBLICATIONS

Wayne Newhauser, Timothy Jones, Stuart Swerdloff, Warren Newhauser, Mark Cilia, Robert Carver, Andy Halloran, Rui Zhang, Anonymization of DICOM electronic medical records for radiation therapy, Computers in Biology and Medicine, vol. 53, 2014, pp. 134-140, (Year: 2014).*

*Primary Examiner* — Joshua B Blanchette
(74) *Attorney, Agent, or Firm* — Baker Botts L.L.P.

(57) ABSTRACT

Method for removing personal data from a medical record includes receiving a first digital medical record associated with a first patient, the first digital medical record including personal data and medical data; generating a first fingerprint by applying a cryptographic function to at least a portion of the personal data; transferring the first fingerprint to one or more computing devices; identifying a first alias associated with the first fingerprint, wherein identifying the first alias includes at least one of determining that the first fingerprint was previously stored along with the first alias, and generating the first alias and storing the first fingerprint and the first alias; transferring the first alias to the workstation of the first user; and generating a first clean digital medical record based on the first alias and the first digital medical record.

21 Claims, 4 Drawing Sheets

(56) References Cited

U.S. PATENT DOCUMENTS

| | | | |
|---|---|---|---|
| 2005/0165623 A1* | 7/2005 | Landi | H04L 9/083 |
| | | | 705/2 |
| 2014/0257047 A1 | 9/2014 | Sillay et al. | |
| 2016/0125138 A1 | 5/2016 | Dorn et al. | |
| 2017/0076046 A1 | 3/2017 | Barnes et al. | |
| 2017/0208041 A1* | 7/2017 | Kho | G16H 10/60 |
| 2017/0255751 A1 | 9/2017 | Sanmugalingham | |
| 2019/0043611 A1 | 2/2019 | Saalbach et al. | |
| 2019/0147988 A1* | 5/2019 | Sharifi Sedeh | G06F 16/22 |
| | | | 705/3 |

* cited by examiner

SYSTEMS AND METHODS FOR REMOVING PERSONAL DATA FROM DIGITAL RECORDS

BACKGROUND

1. Field of Disclosed Subject Matter

The disclosed subject matter is directed to systems and method for removing personal data (also referred to as "personal information" or "personal health information") from digital records, for example, medical image records, and more specifically, Digital Imaging and Communications in Medicine ("DICOM") objects. The systems and methods described herein can remove personal health information from medical image records and replace the personal health information with randomly generated alias information.

2. Description of Related Art

Removing personal information or data from digital records has become popular and important. This is due in part to certain new laws that seek to regulate the storage and transfer of personal information. Additionally, researchers, such as medical researchers, can be interested in studying underlying information stored in digital records of medical studies (i.e., medical data) without reference to specific individuals (i.e., personal data). As an example, medical researchers can seek to study the medical results of one or more patients without needing, wanting, or being permitted to know personal information about the patients. This can occur, for example, when a third party is reviewing the medical results of patients he or she is not affiliated with, when using a large number of results in a machine learning algorithm, or when seeking to publish results.

In medical imaging, Picture Archiving and Communication Systems ("PACS") are a combination of computers and networks dedicated to the storage, retrieval, presentation, and distribution of images. While medical information can be stored in a variety of formats, a common format of image storage is DICOM. DICOM is a standard in which, among other things, medical images and associated meta-data (which can include personal data and medical data) can be communicated from imaging modalities (e.g., x-ray (or x-rays' digital counterparts: computed radiography ("CR") and digital radiography ("DR")), computed tomography ("CT"), and magnetic resonance imaging ("MRI") apparatuses) to remote storage and/or client devices for viewing and/or other use. DICOM records can include personal data and medical data.

Typical tools can replace personal information stored within a record associated with a particular procedure—such as patient name, date of birth, and procedure date—with randomly generated information. However, randomly assigning information to each record can create certain challenges. For example, where a single patient is involved in a number of procedures, it can be important to recognize that the associated records are related (i.e., involve the same patient). This can be important to understand how a patient is healing over time. Therefore, even though a single patient can have two related procedures occur at different times, it can be important that the two corresponding records use the same false patient name and date of birth for analysis purposes. Furthermore, it can be important to understand not just that the records are linked, but how much time has elapsed between records. Accordingly, randomly assigning the procedure date can also cause problems.

Accordingly, there is a need for systems and methods for removing personal data from digital records, including digital medical records and digital medical image records, while allowing identification of related records and elapsed time between related records.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described the disclosed subject matter is directed to systems and methods for removing personal data from digital medical records. For example, a method for removing personal data from a digital medical record includes receiving, at a client device of a first user, a first digital medical record associated with a first patient, the first digital medical record including personal data and medical data; generating, at the client device of the first user, a first fingerprint by applying a cryptographic function to at least a portion of the personal data; transferring the first fingerprint from the workstation of the first user to one or more computing devices; identifying, at the one or more computing devices, a first alias associated with the first fingerprint, wherein identifying the first alias includes at least one of determining that the first fingerprint was previously stored on the one or more computing devices along with the first alias, and generating the first alias and storing the first fingerprint and the first alias on the one or more computing devices; transferring the first alias from the one or more computing devices to the workstation of the first user; and generating, at the workstation of the first user, a first clean digital medical record based on the first alias and the first digital medical record.

The first digital medical record can be a first medical image record and the first clean digital medical record can be a first clean medical image record. The first medical image record can be one or more DICOM Service-Object Pair ("SOP") Instances, and the first clean medical image record can be one or more DICOM SOP Instances.

The cryptographic function can be a cryptographic hash function. The personal data can include personal health information. The personal data can include each of a patient name, a date of birth, and a procedure date. The first alias can include a false patient name and a time-shift variable. The first clean digital medical record can include each of the false patient name; a false date of birth, the false date of birth calculated using the date of birth and the time-shift variable; and a false procedure date, the false procedure date calculated using the procedure date and the time-shift variable.

In accordance with the disclosed subject matter, one or more computer-readable non-transitory storage media embodying software are provided. The software can be operable when executed to: receive, at a client device of a first user, a first digital medical record associated with a first patient, the first digital medical record including personal data and medical data; generate, at the client device of the first user, a first fingerprint by applying a cryptographic function to at least a portion of the personal data; transfer the first fingerprint from the workstation of the first user to one or more computing devices; identify, at the one or more computing devices, a first alias associated with the first fingerprint, wherein to identify the first alias associated with the first fingerprint, the software is operable when executed to at least one of determine that the first fingerprint was previously stored on the one or more computing devices along with the first alias, and generate the first alias and store the first fingerprint and the first alias on the one or more computing devices; transfer the first alias from the one or more computing devices to the workstation of the first user; and generate, at the workstation of the first user, a first clean digital medical record based on the first alias and the first digital medical record.

In accordance with the disclosed subject matter, a system including one or more processors; and a memory coupled to the processors including instructions executable by the processors are provided. The processors can be operable when executing the instructions to: receive, at a client device of a first user, a first digital medical record associated with a first patient, the first digital medical record including personal data and medical data; generate, at the client device of the first user, a first fingerprint by applying a cryptographic function to at least a portion of the personal data; transfer the first fingerprint from the workstation of the first user to one or more computing devices; identify, at the one or more computing devices, a first alias associated with the first fingerprint, wherein to identify the first alias associated with the first fingerprint, the processors are operable when executing instructions to at least one of determine that the first fingerprint was previously stored on the one or more computing devices along with the first alias, and generate the first alias and store the first fingerprint and the first alias on the one or more computing devices; transfer the first alias from the one or more computing devices to the workstation of the first user; and generate, at the workstation of the first user, a first clean digital medical record based on the first alias and the first digital medical record.

DRAWINGS

Figure 3A:
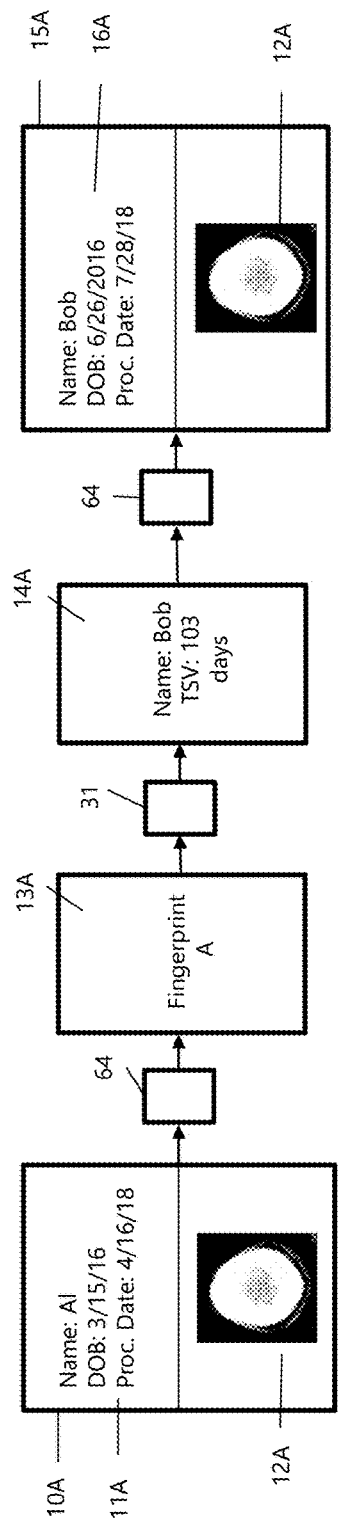
Figure 3B:
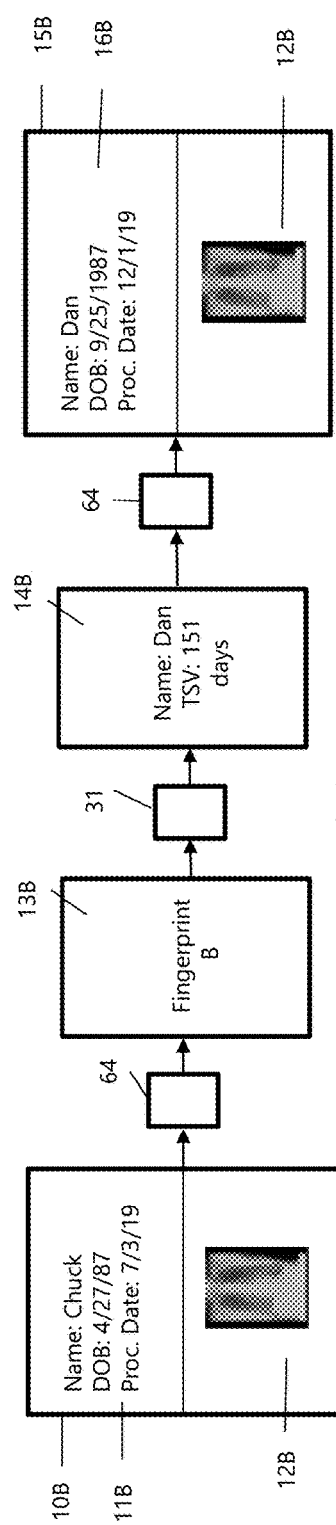
Figure 3C:
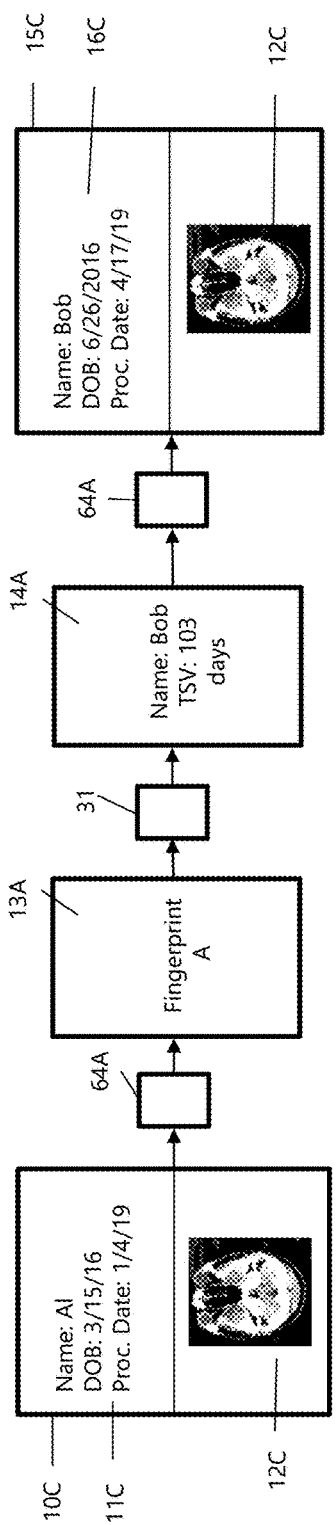

FIGS. 3A-C are flow charts illustrating how personal data can be removed from medical image records in accordance with the disclosed subject matter.

Figure 4:
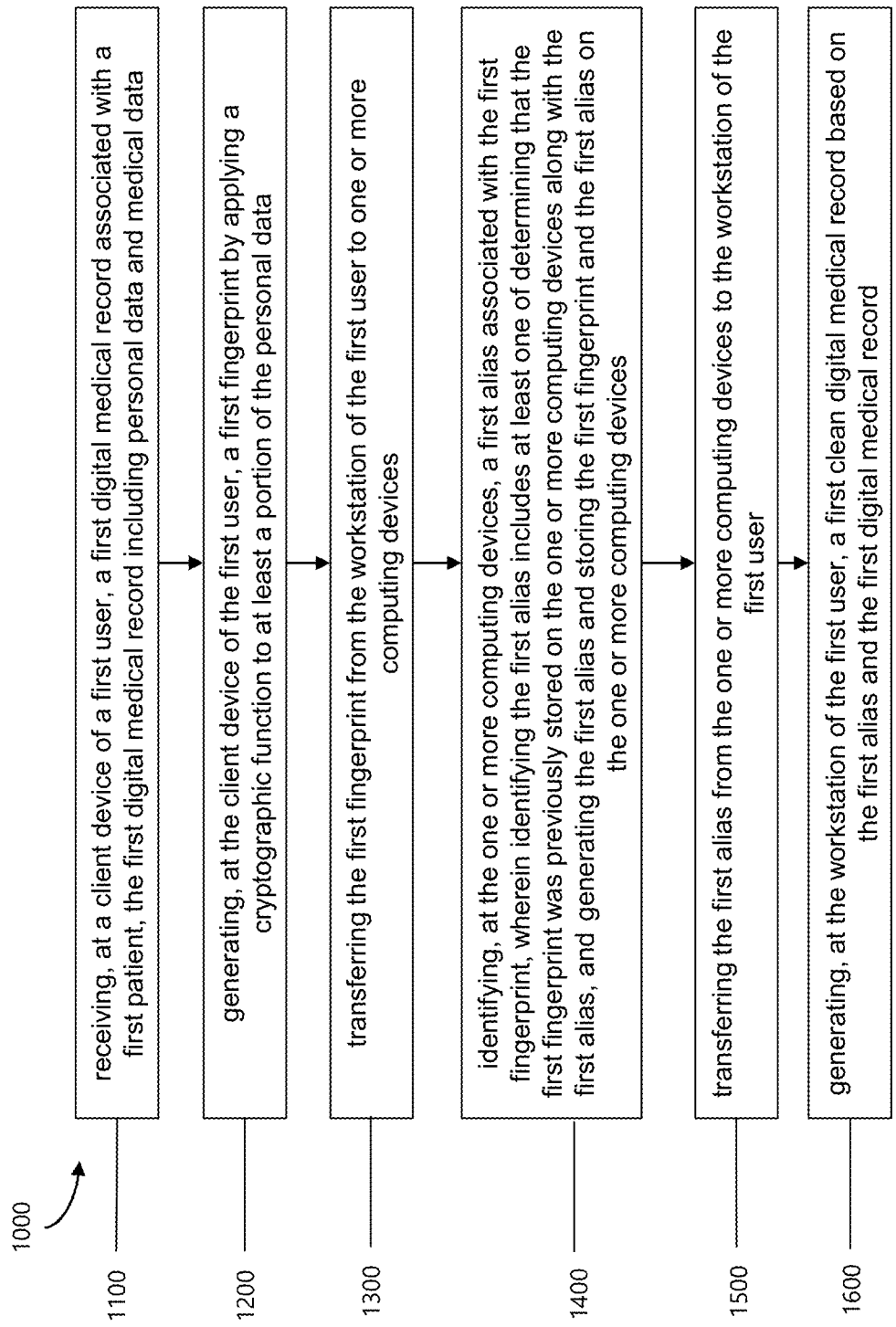

FIG. 4 is a flow chart of a method for removing personal data from a medical record in accordance with the disclosed subject matter.

DETAILED DESCRIPTION

Figure 1:
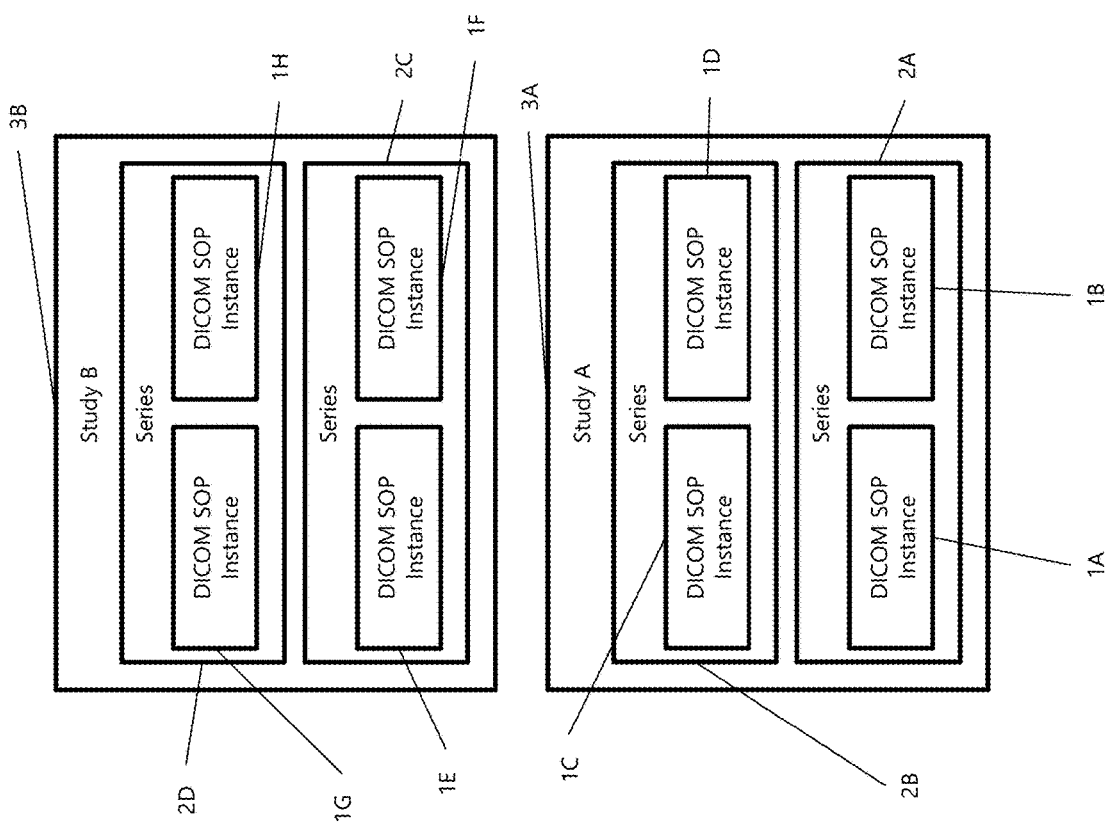
FIG. 1 shows a hierarchy of medical image records that can have personal data removed in accordance with the disclosed subject matter.
Figure 2:
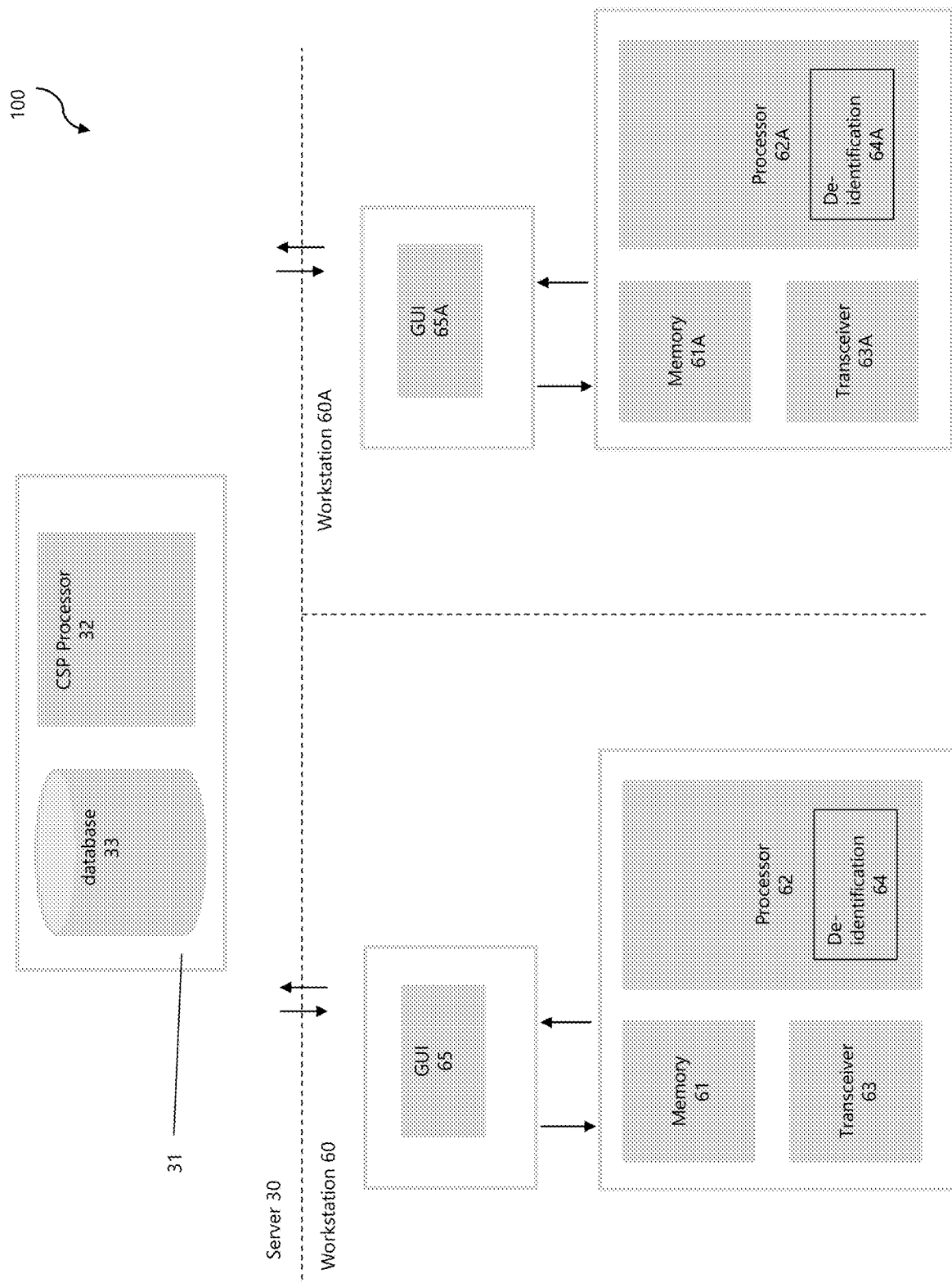
FIG. 2 shows the architecture of a system for removing personal data from medical image records, in accordance with the disclosed subject matter.

Reference will now be made in detail to the various exemplary embodiments of the disclosed subject matter, exemplary embodiments of which are illustrated in the accompanying drawings. For purpose of illustration and not limitation, the systems and method are described herein with respect to removing personal data (also referred to as "personal information" or "personal health information") with respect to digital records, and particularly, digital medical image records (also referred to as "medical image records"), specifically DICOM records. However, the methods and systems described herein can be used for removing personal data from any digital records (medical or otherwise). As used in the description and the appended claims, the singular forms, such as "a," "an," "the," and singular nouns, are intended to include the plural forms as well, unless the context clearly indicates otherwise. Accordingly, as used herein, the term medical image record can refer to one medical image record, or a plurality of medical image records. For example, and with reference to FIG. 1 for purpose of illustration and not limitation, as referred to herein a medical image record can include a single DICOM SOP Instance (also referred to as "DICOM Instance" and "DICOM image") 1 (e.g., 1A-1H), one or more DICOM SOP Instances 1 (e.g., 1A-1H) in one or more Series 2 (e.g., 2A-D), one or more Series 2 (e.g., 2A-D) in one or more Studies 3 (e.g., 3A, 3B), and one or more Studies 3 (e.g., 3A, 3B). The methods and systems described herein can be used with medical image records stored on PACS, however, a variety of records are suitable for the present disclosure and records can be stored in any system, for example a Vendor Neutral Archive ("VNA").

Referring to FIGS. 2 and 3A-C for purpose of illustration and not limitation, the disclosed system 100 can include one or more computing devices defining a server 30 and a user workstation 60. In accordance with the disclosed subject matter, the system 100 can be configured to remove personal data 11 (e.g., 11A-11C) from medical image records 10 (e.g., 10A-10C). The user workstation 60 can be coupled to the server 30 by a network. The network, for example, can be a Local Area Network ("LAN"), a Wireless LAN ("WLAN"), a virtual private network ("VPN"), or any other network that allows for any radio frequency or wireless type connection. For example, other radio frequency or wireless connections can include, but are not limited to, one or more network access technologies, such as Global System for Mobile communication ("GSM"), Universal Mobile Telecommunications System ("UMTS"), General Packet Radio Services ("GPRS"), Enhanced Data GSM Environment ("EDGE"), Third Generation Partnership Project ("3GPP") Technology, including Long Term Evolution ("LTE"), LTE-Advanced, 3G technology, Internet of Things ("IOT"), fifth generation ("5G"), or new radio ("NR") technology. Other examples can include Wideband Code Division Multiple Access ("WCDMA"), Bluetooth, IEEE 802.11b/g/n, or any other 802.11 protocol, or any other wired or wireless connection.

Workstation 60 can take the form of any known client device. For example, workstation 60 can be a computer, such as a laptop or desktop computer, a personal data or digital assistant ("PDA"), or any other user equipment or tablet, such as a mobile device or mobile portable media player. Server 30 can be a service point which provides processing, database, and communication facilities. For example, the server 30 can include dedicated rack-mounted servers, desktop computers, laptop computers, set top boxes, integrated devices combining various features, such as two or more features of the foregoing devices, or the like. Server 30 can vary widely in configuration or capabilities, but can include one or more processors, memory, and/or transceivers. Server 30 can also include one or more mass storage devices, one or more power supplies, one or more wired or wireless network interfaces, one or more input/output interfaces, and/or one or more operating systems.

A user can be any person authorized to access workstation 60 and/or server 30, including a health professional, medical technician, researcher, or patient. In some embodiments a user authorized to use the workstation 60 and/or communicate with the server 30 can have a username and/or password that can be used to login or access workstation 60 and/or server 30.

Workstation 60 can include GUI 65, memory 61, processor 62, and transceiver 63. Medical image records 10 (e.g., 10A-10C) received by workstation 60 can be processed using one or more processors 62. Processor 62 can be any hardware or software used to execute computer program instructions. These computer program instructions can be provided to a processor of a general purpose computer to alter its function to a special purpose, a special purpose computer, application-specific integrated circuit ("ASIC"), or other programmable digital data processing apparatus, such that the instructions, which execute via the processor of the workstation 60 or other programmable data processing apparatus, implement the functions/acts specified in the block diagrams or operational block or blocks, thereby transforming their functionality in accordance with embodiments herein. The processor 62 can be a portable embedded micro-controller or micro-computer. For example, processor 62 can be embodied by any computational or data processing device, such as a central processing unit ("CPU"), digital signal processor ("DSP"), ASIC, programmable logic devices ("PLDs"), field programmable gate arrays ("FPGAs"), digitally enhanced circuits, or comparable device or a combination thereof. The processor 62 can be implemented as a single controller, or a plurality of controllers or processors. Processor 62 can include a de-identification engine 64. Any number of workstations, such as second workstation 60A, each containing one or more features described with regard to workstation 60, can be coupled to the server 30. For example, second workstation 60A can be a different workstation than the workstation 60, but similarly or differently configured (wherein like features are labeled with like numbers). That is, second workstation 60A can include a second memory 61A, second processor 62A including a second de-identification module 64A, a second transceiver 63A, and a second GUI 65A.

The de-identification engine 64 can be configured to perform a cryptographic function on medical image records 10 (e.g., 10A-10C) received by workstation 60 to generate a fingerprint 13 (e.g., 13A, 13B). The fingerprint 13 (e.g., 13A, 13B) can be unique for a unique patient information combination, such as the name and date of birth of the patient. Accordingly, where two medical image records 10 (e.g., 10A-10C) include the same patient name and date of birth, the fingerprint 13 (e.g., 13A, 13B) generated by de-identification engine 64 can be identical. Where two medical image records 10 (e.g., 10A-10C) include any difference in patient name and/or date of birth, the fingerprints 13 (e.g., 13A, 13B) generated by de-identification engine 64 can be different. For example, and as shown in FIGS. 3A-C for purpose of illustration and not limitation, medical image records 10A and 10C have the same patient name (Al) and date of birth (Mar. 15, 2016), and therefore de-identification engine 64 generates the same fingerprint 13A based on medical image records 10A and 10C. In contrast, medical image record 10B has a different patient name (Chuck) and date of birth (Apr. 27, 1987) and therefore de-identification engine 64 generates a different fingerprint 13B based on medical image record 10B. The cryptographic function can be a cryptographic hash function, which can be a one-way encryption. That is, while information stored in the medical image record 10 (e.g., 10A-10C) can be used to generate the fingerprint 13 (e.g., 13A, 13B), the fingerprint 13 (e.g., 13A, 13B) cannot be used to determine (e.g., reverse engineer) the information stored in the medical image records 10 (e.g., 10A-10C). The fingerprint 13 (e.g., 13A, 13B) can be any format of data that the computing architecture allows. De-identification engine 64 can further generate clean medical image records 15 (e.g., 15A, 15B, 15C) using an aliases 14 (e.g., 14A, 14B) provided by the consistency service provider 31 (as described in greater detail below).

Workstation 60 can send and receive medical image records 10 (e.g., 10A-10C), fingerprints 13 (e.g., 13A, 13B), and aliases 14 (e.g., 14A, 14B) from server 30 using transceiver 63. Transceiver 63 can, independently, be a transmitter, a receiver, or both a transmitter and a receiver, or a unit or device that can be configured both for transmission and reception. In other words, transceiver 63 can include any hardware or software that allows workstation 60 to communicate with server 30. Transceiver 63 can be either a wired or a wireless transceiver. When wireless, the transceiver 63 can be implemented as a remote radio head which is not located in the device itself, but in a mast. While FIG. 2 only illustrates a single transceiver 63, workstation 60 can include one or more transceivers 63. Memory 61 can be a non-volatile storage medium or any other suitable storage device, such as a non-transitory computer-readable medium or storage medium. For example, memory 61 can be a random-access memory ("RAM"), read-only memory ("ROM"), hard disk drive ("HDD"), erasable programmable read-only memory ("EPROM"), electrically erasable programmable read-only memory ("EEPROM"), flash memory or other solid-state memory technology. Memory 61 can also be a compact disc read-only optical memory ("CD-ROM"), digital versatile disc ("DVD"), any other optical storage, magnetic cassettes, magnetic tape, magnetic disk storage or other magnetic storage devices, or any other physical or material medium which can be used to tangibly store the desired information or data or instructions and which can be accessed by a computer or processor. Memory 61 can be either removable or non-removable.

Server 30 can include a consistency service provider ("CSP") 31, which can include a database 33 and CSP processor 32. The CSP processor 32 can be any hardware or software used to execute computer program instructions. These computer program instructions can be provided to a processor of a general purpose computer to alter its function to a special purpose, a special purpose computer, ASIC, or other programmable digital data processing apparatus, such that the instructions, which execute via the processor of the client station or other programmable data processing apparatus, implement the functions/acts specified in the block diagrams or operational block or blocks, thereby transforming their functionality in accordance with embodiments herein. In accordance with the disclosed subject matter, the CSP processor 32 can be a portable embedded micro-controller or micro-computer. For example, CSP processor 32 can be embodied by any computational or data processing device, such as a CPU, DSP, ASIC, PLDs, FPGAs, digitally enhanced circuits, or comparable device or a combination thereof. The CSP processor 32 can be implemented as a single controller, or a plurality of controllers or processors. Database 33 can store fingerprints 13 (e.g., 13A, 13B) and aliases 14 (e.g., 14A, 14B).

CSP 31 can identify an alias 14 (e.g., 14A, 14B) associated with a fingerprint 13 (e.g., 13A, 13B) received from the workstation 60. Identifying an alias 14 (e.g., 14A, 14B) associated with a fingerprint 13 (e.g., 13A, 13B) can include determining that the fingerprint 13 (e.g., 13A, 13B) and alias 14 (e.g., 14A, 14B) were previously stored, for example, in database 33, and accessing the fingerprint 13 (e.g., 13A, 13B) and alias 14 (e.g., 14A, 14B) from database 33. Alternatively, alias 14 (e.g., 14A, 14B) can be generated using random generators to create a false patient name and a time-shift variable ("TSV"). The alias 14 (e.g., 14A, 14B) can include a time-shift variable so that when a patient undergoes two or more procedures, the dates of the procedures can be shifted by the same amount of time. As a result, the relative date of the procedures can remain the same. Put another way, the time between the procedures is maintained. Additionally, the age of the patient at the time of each procedure can remain constant, because the date of birth of the patient can also be shifted by the time-shift variable. The CSP 31 can select a positive value for the time-shift variable, so that dates are shifted into the future. Furthermore, because the approximate age of a patient in a study can be important (e.g., if 10 years are added to 2-year-old, the corresponding medical data can lose significant value), limits can be placed on the range of randomness used to generate the time-shift variable. For example, the time-shift variable can be limited zero to one year or zero to five years. The range of randomness can be limited based on the age of the patient. Limits can be preconfigured based on rules for a specified age range. For example, for infants the range of randomness can be less than one year, while for teenagers the range of randomness can be less than five years. The patient's age can be determined using DICOM attributes or by calculating using the patient's date of birth and the procedure date. The identified alias 14 (e.g., 14A, 14B) can be sent to workstation 60.

In operation, workstation 60 can receive a request to clean a medical image record 10 (e.g., 10A-10C). For example, and with reference to FIG. 3A, for purpose of illustration and not limitation, the medical image record 10A can include personal data 11A and medical data 12A. The medical data 12A can include one or more medical images, such as CT brain scans. The personal data 11A can include a patient name, date of birth, and procedure date. For example, as shown in FIG. 3A, medical image record 10A includes a patient name of Al, a date of birth of Mar. 15, 2016, and a procedure date of Apr. 16, 2018. De-identification module 64 can generate a fingerprint 13A based on at least a portion of the personal data 11A in the medical image record 10A. For example, the fingerprint 13A can be generated using a cryptographic hash function based on the patient name and date of birth. The fingerprint 13A can be transferred to CSP 31 on server 30. The CSP 31 can identify an alias 14A associated with the fingerprint 13A. To identify alias 14A, CSP 31 can first check database 33 to determine if the fingerprint 13A was previously stored in database 33, along with the alias 14A. If fingerprint 13A and alias 14A were not previously received by CSP 31 and stored in database 33 (as is the example in FIG. 3A), CSP 31 can generate alias 14A. For example, CSP 31 can randomly generate a patient name, which is a false patient name, and a time-shift variable. For example, as shown in FIG. 3A, alias 14A includes a patient name Bob and a time-shift variable of 103 days. The alias 14A and fingerprint 13A can be stored in database 33 and the alias 14A can be transferred from the CSP 31 to the workstation 60. The de-identification module 64 can generate a clean medical image record 15A using the alias 14A and the medical image record 10A. For example, and as shown in FIG. 3A, the clean medical image record 15A can have false personal data 16A including patient name Bob, date of birth of Jun. 26, 2016 (i.e., Mar. 15, 2016 shifted forward 103 days) and procedure date of Jul. 28, 2018 (i.e., Apr. 16, 2018 shifted forward 103 days). Accordingly, the relative age of the patient at the procedure date remains constant. The clean medical image record 15A can also include medical data 12A, which can be the same as medical data 12A in medical image record 10A.

With reference to FIG. 3B, for purpose of illustration and not limitation, workstation 60 can receive a request to clean medical image record 10B. The method of cleaning medical image record 10B can proceed as described above with regard to medical image record 10A. Particularly, medical image record 10B can include personal data 11B and medical data 12B. The medical data 12B can include one or more medical images, such as chest CR images. The personal data 11B can include a patient name of Chuck, a date of birth of Apr. 27, 1987, and a procedure date of Jul. 3, 2019. De-identification module 64 can generate fingerprint 13B based on at least a portion of the personal data 11B in the medical image record 10B, as described above. The fingerprint 13B is different than fingerprint 13A because the personal data 11B in medical image record 10B used by de-identification module 64 is different than the personal data 11A in medical image record 10A used by de-identification module 64. Fingerprint 13B can be transferred to CSP 31 on server 30. CSP 31 can identify an alias 14B associated with fingerprint 13B. To identify alias 14B, CSP 31 can first check database 33 to determine if the fingerprint 13B was previously stored in database 33, along with alias 14B. If fingerprint 13B and alias 14B were not previously received by CSP 31 and stored in database 33 (as is the example in FIG. 3B), CSP 31 can generate alias 14B. For example, CSP 31 can randomly generate a patient name, which is a false patient name, and a time-shift variable. For example, as shown in FIG. 3B, alias 14B includes a patient name Dan and a time-shift variable of 151 days. The alias 14B and fingerprint 13B can be stored in database 33 and the alias 14B can be transferred from the CSP 31 to the workstation 60. The de-identification module 64 can generate a clean medical image record 15B using the alias 14B and the medical image record 10B. For example, and as shown in FIG. 3B, the clean medical image record 10B can include false personal data 16B including patient name Dan, date of birth of Sep. 25, 1987 (i.e., Apr. 27, 1987 shifted forward 151 days) and procedure date of Dec. 1, 2019 (i.e., Jul. 3, 2019 shifted forward 151 days). Accordingly, the relative age of the patient at the procedure date remains constant. The clean medical image record 15B can also include medical data 12B, which can be the same as medical data 12B in medical image record 10B.

With reference to FIG. 3C, for purpose of illustration and not limitation, second workstation 60A can receive a request to clean medical image record 10C. Second workstation 60A can communicate with server 30 and CSP 31 as described above with regard to workstation 60. The method of cleaning medical image record 10C can proceed as described above. Particularly, medical image record 10C can include personal data 11C and medical data 12C. The medical data 12C can include one or more medical images, such as CT brain scans. The personal data 11C can include a patient name of Al, date of birth of Mar. 15, 2016, and a procedure date of Jan. 4, 2019. As shown in FIGS. 3A and 3C, medical image record 10C and medical image record 10A include the same patient name and date of birth, and are associated with two medical procedures for the same patient (Al) that occur on different days. Second de-identification module 64A can generate fingerprint 13A based on at least a portion of the personal data 11C in the medical image record 10C, as described above. Because medical image records 10C and 10A include the same patient name and date of birth, the fingerprint 13A generated based on medical image record 10C is the same as fingerprint 13A generated based on medical image record 10A. Indeed any de-identification module (e.g., 64, 64A) can generate the same fingerprint 13A when the input is the same (e.g., patient name and date of birth). Fingerprint 13C can be transferred to CSP 31 on server 30, which can be the same server 30 and CSP 31 described above with regard to FIGS. 3A and 3B. CSP 31 can identify an alias 14A associated with fingerprint 13A. To identify alias 14A, CSP 31 can check database 33 to determine if fingerprint 13A was previously stored in database 33 along with alias 14A (as is the example in FIG. 3C). Because fingerprint 13A was previously received by CSP 31, alias 14A was previously generated (as described in above with regard to FIG. 3A), and both fingerprint 13A and alias 14A were previously stored in database 33. Accordingly, CSP 31 can access alias 14A from database 33. Alias 14A can be transferred from the CSP 31 to second workstation 60A, and the second de-identification module 64A can generate a clean medical image record 15C using the alias 14A and the medical image record 10C. For example, and as shown in FIG. 3C, the clean medical image record 15C can include false personal data 16C, including patient name Bob, date of birth Jun. 26, 2016, and procedure date of Apr. 17, 2019 (i.e., Jan. 4, 2019 shifted forward 103 days). Accordingly, the relative age of the patient at the procedure date remains constant. The clean medical image record 15C can also include medical data 12C, which can be the same as medical data 12C in medical image record 10C.

As shown in FIGS. 3A and 3C, clean medical image records 15A and 15C include the same false patient name (Bob) and the same date of birth Jun. 26, 2016 (i.e., Mar. 15, 2016 shifted forward 103 days). Accordingly, a user can determine that the clean medical image records 15A and 15C are associated with one another even though clean medical image records 15A and 15C include a false patient name and a false date of birth. This occurs because medical image records 10A and 10C include the same patient name and date of birth and therefore the same fingerprint 13A was created for each medical image record 10A and 10C. Accordingly, CSP 31 identified the same alias 14A for medical image records 10A and 10C, first by generating alias 14A (FIG. 3A) and second by determining that fingerprint 13A and alias 14A were previously stored in database 33 (FIG. 3C). Alias 14A was therefore used to generate clean medical image record 15A and 15C. Additionally, because alias 14A includes a time-shift variable (103 days) the date of birth and each procedure date were shifted forward by the time-shift variable. Accordingly, the number of days between the procedure dates for clean medical image records 15A and 15C (263 days; i.e., the time between Jul. 28, 2018 and Apr. 17, 2019), is the same as the number of days between the procedure dates for medical image records 10A and 10C (263 days; i.e., the time between Apr. 16, 2018 and Jan. 4, 2019). By contrast, clean medical image record 15B in FIG. 3B, which is generated based on medical image record 10B (and a different patient than the patient of medical image records 10A and 10C), includes a different name and date of birth.

FIG. 4 illustrates an example method 1000 for removing personal data from a medical record. The method can begin at step 1100, where the method includes receiving, at a client device of a first user, a first digital medical record associated with a first patient, the first digital medical record including personal data and medical data. At step 1200 the method can include generating, at the client device of the first user, a first fingerprint by applying a cryptographic function to at least a portion of the personal data. At step 1300 the method can include transferring the first fingerprint from the workstation of the first user to one or more computing devices. At step 1400 the method can include identifying, at the one or more computing devices, a first alias associated with the first fingerprint, wherein identifying the first alias includes at least one of determining that the first fingerprint was previously stored on the one or more computing devices along with the first alias, and generating the first alias and storing the first fingerprint and the first alias on the one or more computing devices. At step 1500 the method can include transferring the first alias from the one or more computing devices to the workstation of the first user. At step 1600 the method can include generating, at the workstation of the first user, a first clean digital medical record based on the first alias and the first digital medical record. In accordance with the disclosed subject matter, the method can repeat one or more steps of the method of FIG. 4, where appropriate. Although this disclosure describes and illustrates particular steps of the method of FIG. 4 as occurring in a particular order, this disclosure contemplates any suitable steps of the method of FIG. 4 occurring in any suitable order. Moreover, although this disclosure describes and illustrates an example method for removing personal data from a medical record including the particular steps of the method of FIG. 4, this disclosure contemplates any suitable method for removing personal data from a medical record including any suitable steps, which can include all, some, or none of the steps of the method of FIG. 4, where appropriate. Furthermore, although this disclosure describes and illustrates particular components, devices, or systems carrying out particular steps of the method of FIG. 4, this disclosure contemplates any suitable combination of any suitable components, devices, or systems carrying out any suitable steps of the method of FIG. 4.

As described above in connection with certain embodiments, certain components, e.g., server 30 and workstation (e.g., 60, 60A), can include a computer or computers, processor, network, mobile device, cluster, or other hardware to perform various functions. Moreover, certain elements of the disclosed subject matter can be embodied in computer readable code which can be stored on computer readable media and which when executed can cause a processor to perform certain functions described herein. In these embodiments, the computer and/or other hardware play a significant role in permitting the system and method for displaying medical image records. For example, the presence of the computers, processors, memory, storage, and networking hardware provides the ability to display medical image records in a more efficient manner. Moreover, the display of medical image records, cannot be accomplished with pen or paper, as such information is received over a network in electronic form.

The subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificiallygenerated propagated signal. The computer storage medium also can be, or may be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA or an ASIC. The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program can, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program can include, by way of example and not by way of limitation, both general and special purpose microprocessors. Devices suitable for storing computer program instructions and data can include all forms of non-volatile memory, media and memory devices, including by way of example but not by way of limitation, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Additionally, as described above in connection with certain embodiments, certain components can communicate with certain other components, for example via a network, e.g., a local area network or the internet. To the extent not expressly stated above, the disclosed subject matter is intended to encompass both sides of each transaction, including transmitting and receiving. One of ordinary skill in the art will readily understand that with regard to the features described above, if one component transmits, sends, or otherwise makes available to another component, the other component will receive or acquire, whether expressly stated or not.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A method for removing personal data from a medical record, comprising:
   receiving, at a client device of a first user, a first digital medical record associated with a first patient, the first digital medical record including personal data and medical data;
   generating, at the client device of the first user, a first fingerprint by applying a cryptographic function to at least a portion of the personal data;
   transferring the first fingerprint from the workstation of the first user to one or more computing devices;
   identifying, at the one or more computing devices, a first alias associated with the first fingerprint, wherein identifying the first alias includes at least one of
      determining that the first fingerprint was previously stored on the one or more computing devices along with the first alias, and
      generating the first alias and storing the first fingerprint and the first alias on the one or more computing devices,
      wherein the first alias comprises a time-shift variable generated by a random generator, the time-shift variable limited to a range of randomness determined based on an age of the first patient;
   transferring the first alias from the one or more computing devices to the workstation of the first user; and
   generating, at the workstation of the first user, a first clean digital medical record based on the first alias and the first digital medical record;
   wherein the first digital medical record comprises one or more Digital Imaging and Communications in Medicine ("DICOM") Service-Object Pair ("SOP") Instances, and the first clean digital medical record comprises one or more DICOM SOP Instances.

2. The method of claim 1, wherein the first digital medical record comprises a first medical image record and the first clean digital medical record comprises a first clean medical image record.

3. The method of claim 1, wherein the cryptographic function is a cryptographic hash function.

4. The method of claim 1, wherein the personal data comprises personal health information.

5. The method of claim 1, wherein the personal data comprises each of a patient name, a date of birth, and a procedure date.

6. The method of claim 5, wherein the first alias further comprises a false patient name.

7. The method of claim 6, wherein the first clean digital medical record comprises each of
the false patient name;
a false date of birth, the false date of birth calculated using the date of birth and the time-shift variable; and
a false procedure date, the false procedure date calculated using the procedure date and the time-shift variable.

8. One or more computer-readable non-transitory storage media embodying software that is operable when executed to:
receive, at a client device of a first user, a first digital medical record associated with a first patient, the first digital medical record including personal data and medical data;
generate, at the client device of the first user, a first fingerprint by applying a cryptographic function to at least a portion of the personal data;
transfer the first fingerprint from the workstation of the first user to one or more computing devices;
identify, at the one or more computing devices, a first alias associated with the first fingerprint, wherein to identify the first alias associated with the first fingerprint, the software is operable when executed to at least one of
determine that the first fingerprint was previously stored on the one or more computing devices along with the first alias, and
generate the first alias and store the first fingerprint and the first alias on the one or more computing devices,
wherein the first alias comprises a time-shift variable generated by a random generator, the time-shift variable limited to a range of randomness determined based on an age of the first patient;
transfer the first alias from the one or more computing devices to the workstation of the first user; and
generate, at the workstation of the first user, a first clean digital medical record based on the first alias and the first digital medical record;
wherein the first digital medical record comprises one or more Digital Imaging and Communications in Medicine ("DICOM") Service-Object Pair ("SOP") Instances, and the first clean digital medical record comprises one or more DICOM SOP Instances.

9. The media of claim 8, wherein the first digital medical record comprises a first medical image record and the first clean digital medical record comprises a first clean medical image record.

10. The media of claim 8, wherein the cryptographic function is a cryptographic hash function.

11. The media of claim 8, wherein the personal data comprises personal health information.

12. The media of claim 8, wherein the personal data comprises each of a patient name, a date of birth, and a procedure date.

13. The media of claim 12, wherein the first alias further comprises a false patient name.

14. The media of claim 13, wherein the first clean digital medical record comprises each of
the false patient name;
a false date of birth, the false date of birth calculated using the date of birth and the time-shift variable; and
a false a procedure date, the false procedure date calculated using the procedure date and the time-shift variable.

15. A system comprising: one or more processors; and a memory coupled to the processors comprising instructions executable by the processors, the processors being operable when executing the instructions to:
receive, at a client device of a first user, a first digital medical record associated with a first patient, the first digital medical record including personal data and medical data;
generate, at the client device of the first user, a first fingerprint by applying a cryptographic function to at least a portion of the personal data;
transfer the first fingerprint from the workstation of the first user to one or more computing devices;
identify, at the one or more computing devices, a first alias associated with the first fingerprint, wherein to identify the first alias associated with the first fingerprint, the processors are operable when executing instructions to at least one of
determine that the first fingerprint was previously stored on the one or more computing devices along with the first alias, and
generate the first alias and store the first fingerprint and the first alias on the one or more computing devices,
wherein the first alias comprises a time-shift variable generated by a random generator, the time-shift variable limited to a range of randomness determined based on an age of the first patient;
transfer the first alias from the one or more computing devices to the workstation of the first user; and
generate, at the workstation of the first user, a first clean digital medical record based on the first alias and the first digital medical record;
wherein the first digital medical record comprises one or more Digital Imaging and Communications in Medicine ("DICOM") Service-Object Pair ("SOP") Instances, and the first clean digital medical record comprises one or more DICOM SOP Instances.

16. The system of claim 15, wherein the first digital medical record comprises a first medical image record and the first clean digital medical record comprises a first clean medical image record.

17. The system of claim 15, wherein the cryptographic function is a cryptographic hash function.

18. The system of claim 15, wherein the personal data comprises personal health information.

19. The system of claim 15, wherein the personal data comprises each of a patient name, a date of birth, and a procedure date.

20. The system of claim 19, wherein the first alias further comprises a false patient name.

21. The system of claim 20, wherein the first clean digital medical record comprises each of
the false patient name;
a false date of birth, the false date of birth calculated using the date of birth and the time-shift variable; and
a false procedure date, the false procedure date record calculated using the procedure date and the time-shift variable.

* * * * *